(12) United States Patent
Fraden

(10) Patent No.: US 7,828,743 B2
(45) Date of Patent: Nov. 9, 2010

(54) MEDICAL BODY CORE THERMOMETER

(75) Inventor: Jacob Fraden, San Diego, CA (US)

(73) Assignee: Advanced Monitors Corporation, San Diego, CA (US)

( * ) Notice: Subject to any disclaimer, the term of this patent is extended or adjusted under 35 U.S.C. 154(b) by 59 days.

(21) Appl. No.: 11/564,449

(22) Filed: Nov. 29, 2006

(65) Prior Publication Data

US 2007/0100564 A1    May 3, 2007

Related U.S. Application Data

(63) Continuation of application No. PCT/US2005/004884, filed on Feb. 16, 2005, which is a continuation-in-part of application No. 10/870,654, filed on Jun. 18, 2004.

(60) Provisional application No. 60/495,952, filed on Aug. 19, 2003.

(51) Int. Cl.
*A61B 5/00* (2006.01)

(52) U.S. Cl. ......................................... 600/549; 702/22

(58) Field of Classification Search ................. 600/549, 600/475, 474; 374/164, 133; 364/557
See application file for complete search history.

(56) References Cited

U.S. PATENT DOCUMENTS

| | | |
|---|---|---|
| 3,156,117 A | 11/1964 | Benzinger |
| 3,531,992 A | 10/1970 | Moore |
| 3,570,312 A | 3/1971 | Kreith |
| 3,681,991 A | 8/1972 | Eberly, Jr. |
| 3,832,902 A | 9/1974 | Usami et al. |
| 3,872,726 A | 3/1975 | Kauffeld et al. |
| 3,893,058 A | 7/1975 | Keith |

(Continued)

FOREIGN PATENT DOCUMENTS

CH        514834 C2      4/2001

(Continued)

OTHER PUBLICATIONS

U.S. Patent and Trademark Office, International Search Report and Written Opinion in corresponding PCT/US2005/004884, Oct. 14, 2005.

(Continued)

*Primary Examiner*—Max Hindenburg
*Assistant Examiner*—Fangemonique Smith
(74) *Attorney, Agent, or Firm*—Wood, Herron & Evans, LLP

(57) ABSTRACT

A temperature sensing device accurately determines the core temperature of a warm blooded animal or human based on at least one measurement of the temperature of the skin of the warm blooded animal or human. The device includes a housing, and a first contact type temperature sensing element coupled to the housing. The first contact type temperature sensing element includes a first temperature sensor that is operative to measure the temperature of the skin when the first contact type temperature sensing element is in contact with the skin. The first temperature sensor produces at least a first signal representative of the measured skin temperature. An electronic circuit uses the first signal to determine the core temperature of the warm blooded animal or human. An electronic communication device, such as a display, is coupled to the electronic circuit for communicating the core temperature to a user.

18 Claims, 4 Drawing Sheets

U.S. PATENT DOCUMENTS

| | | |
|---|---|---|
| 3,903,744 A | 9/1975 | Cone |
| 3,933,045 A | 1/1976 | Fox et al. |
| 3,935,744 A | 2/1976 | Beckman |
| 3,942,123 A | 3/1976 | Georgi |
| 3,946,613 A | 3/1976 | Silver |
| 3,949,609 A | 4/1976 | Hammerslag |
| 3,978,325 A | 8/1976 | Goldstein et al. |
| 4,009,615 A | 3/1977 | Ruhl |
| 4,022,063 A | 5/1977 | West et al. |
| 4,068,526 A | 1/1978 | Goldstein |
| 4,158,965 A | 6/1979 | Prosky |
| 4,161,880 A | 7/1979 | Prosky |
| 4,166,389 A | 9/1979 | Montren |
| 4,183,248 A | 1/1980 | West |
| 4,204,429 A | 5/1980 | Shimazaki et al. |
| 4,411,535 A | 10/1983 | Schwarzschild |
| 4,439,290 A | 3/1984 | Marfurt et al. |
| 4,444,517 A | 4/1984 | Murase |
| 4,454,370 A | 6/1984 | Voznick |
| 4,457,633 A | 7/1984 | Andrews |
| 4,461,584 A | 7/1984 | Murase |
| 4,464,067 A | 8/1984 | Hanaoka |
| 4,487,208 A | 12/1984 | Kamens |
| 4,503,862 A | 3/1985 | Baessler |
| 4,536,851 A | 8/1985 | Germanton et al. |
| 4,537,518 A | 8/1985 | Murase |
| 4,539,994 A | 9/1985 | Baumbach et al. |
| 4,541,734 A | 9/1985 | Ishizaka |
| 4,549,819 A | 10/1985 | Muramoto et al. |
| 4,572,365 A | 2/1986 | Bruno et al. |
| 4,588,306 A | 5/1986 | Burger et al. |
| 4,602,871 A | 7/1986 | Hanaoka |
| 4,619,271 A | 10/1986 | Burger et al. |
| 4,629,336 A | 12/1986 | Ishizaka |
| 4,636,091 A | 1/1987 | Pompei et al. |
| 4,648,055 A | 3/1987 | Ishizaka et al. |
| 4,651,750 A | 3/1987 | Northeved |
| 4,691,713 A | 9/1987 | Suzuki |
| 4,729,672 A | 3/1988 | Takagi |
| 4,763,522 A | 8/1988 | Pompei |
| 4,843,577 A | 6/1989 | Muramoto |
| 4,846,583 A | 7/1989 | Yamamoto |
| 4,863,279 A | 9/1989 | Markel et al. |
| 4,863,281 A * | 9/1989 | Suszynski ............... 374/158 |
| 4,866,621 A | 9/1989 | Ono |
| 4,874,253 A | 10/1989 | Pompei et al. |
| 4,877,333 A | 10/1989 | Ota et al. |
| 4,880,076 A | 11/1989 | Ahlberg et al. |
| 4,898,022 A * | 2/1990 | Yumoto et al. ............... 73/46 |
| 4,930,222 A | 6/1990 | Nakanishi et al. |
| 4,987,579 A | 1/1991 | Yoshinaka et al. |
| 4,993,419 A | 2/1991 | Pompei et al. |
| 5,011,294 A | 4/1991 | Yamaguchi |
| 5,012,813 A | 5/1991 | Pompei et al. |
| 5,017,019 A | 5/1991 | Pompei |
| 5,050,612 A | 9/1991 | Matsumura |
| 5,056,048 A | 10/1991 | Seperant |
| 5,062,432 A | 11/1991 | James et al. |
| 5,088,836 A | 2/1992 | Yamada et al. |
| 5,088,837 A | 2/1992 | Shiokawa et al. |
| 5,116,136 A | 5/1992 | Newman et al. |
| 5,126,937 A | 6/1992 | Yamaguchi et al. |
| 5,149,200 A | 9/1992 | Shiokawa et al. |
| 5,150,969 A | 9/1992 | Goldberg et al. |
| 5,178,468 A | 1/1993 | Shiokawa et al. |
| 5,183,337 A | 2/1993 | Pompei |
| 5,199,436 A | 4/1993 | Pompei et al. |
| 5,215,100 A * | 6/1993 | Spitz et al. ............... 600/554 |
| 5,259,389 A | 11/1993 | Muramoto et al. |
| 5,271,407 A | 12/1993 | Pompei et al. |
| 5,295,746 A | 3/1994 | Friauf et al. |
| 5,325,863 A | 7/1994 | Pompei |
| 5,333,622 A | 8/1994 | Casali et al. |
| 5,333,784 A | 8/1994 | Pompei |
| 5,340,215 A * | 8/1994 | Makita et al. ............... 374/121 |
| 5,381,796 A | 1/1995 | Pompei |
| 5,445,158 A | 8/1995 | Pompei |
| 5,469,855 A | 11/1995 | Pompei et al. |
| D370,860 S | 6/1996 | Pompei et al. |
| 5,628,323 A | 5/1997 | Pompei |
| 5,632,555 A | 5/1997 | Gregory et al. |
| RE035,554 E | 7/1997 | Pompei et al. |
| 5,642,735 A | 7/1997 | Kolbly |
| 5,653,238 A | 8/1997 | Pompei |
| 5,653,239 A | 8/1997 | Pompei et al. |
| 5,655,305 A | 8/1997 | Fletcher |
| 5,673,692 A | 10/1997 | Schulze et al. |
| 5,674,009 A * | 10/1997 | Stark ............... 374/209 |
| 5,688,266 A | 11/1997 | Edwards et al. |
| 5,725,308 A | 3/1998 | Smith et al. |
| 5,732,711 A | 3/1998 | Fitzpatrick et al. |
| 5,743,648 A | 4/1998 | Zeindler |
| 5,783,833 A | 7/1998 | Sugaya et al. |
| 5,836,692 A | 11/1998 | Pompei |
| 5,874,736 A | 2/1999 | Pompei |
| 5,893,833 A | 4/1999 | Pompei et al. |
| 5,894,126 A | 4/1999 | Pompei et al. |
| 5,897,552 A | 4/1999 | Edwards et al. |
| 6,000,846 A | 12/1999 | Gregory et al. |
| 6,036,361 A | 3/2000 | Gregory et al. |
| 6,045,257 A | 4/2000 | Pompei et al. |
| 6,047,205 A | 4/2000 | Pompei |
| 6,048,902 A | 4/2000 | Lebwohl et al. |
| 6,056,435 A | 5/2000 | Pompei |
| 6,059,452 A | 5/2000 | Smith et al. |
| 6,068,399 A | 5/2000 | Tseng |
| 6,074,090 A | 6/2000 | Chen |
| 6,146,015 A | 11/2000 | Weiss |
| 6,179,785 B1 | 1/2001 | Martinosky et al. |
| 6,219,573 B1 | 4/2001 | Pompei |
| 6,220,750 B1 | 4/2001 | Palti |
| 6,241,384 B1 | 6/2001 | Pompei et al. |
| 6,250,802 B1 | 6/2001 | Dotan |
| 6,257,758 B1 | 7/2001 | Culbertson |
| 6,280,397 B1 | 8/2001 | Yarden et al. |
| 6,283,915 B1 | 9/2001 | Aceti et al. |
| 6,292,685 B1 | 9/2001 | Pompei |
| 6,299,347 B1 | 10/2001 | Pompei |
| 6,319,206 B1 | 11/2001 | Pompei et al. |
| 6,402,371 B2 | 6/2002 | Pompei et al. |
| 6,419,388 B2 | 7/2002 | Lee |
| 6,450,970 B1 | 9/2002 | Mahler et al. |
| 6,499,877 B2 | 12/2002 | Pompei |
| 6,522,912 B1 | 2/2003 | Nakatani et al. |
| 6,547,744 B1 | 4/2003 | Pompei et al. |
| 6,556,852 B1 | 4/2003 | Schulze et al. |
| 6,629,776 B2 | 10/2003 | Bell et al. |
| 6,641,301 B2 | 11/2003 | Pompei |
| 6,794,990 B2 | 9/2004 | Tseng |
| 6,827,487 B2 | 12/2004 | Baumbach |
| 6,830,549 B2 | 12/2004 | Bui et al. |
| 6,839,651 B2 | 1/2005 | Lantz et al. |
| 6,854,882 B2 | 2/2005 | Chen |
| 2001/0025151 A1 | 9/2001 | Kimball et al. |
| 2002/0010390 A1 | 1/2002 | Guice et al. |
| 2002/0114375 A1 | 8/2002 | Pompei |
| 2002/0138017 A1 | 9/2002 | Bui et al. |
| 2002/0150143 A1 | 10/2002 | Tokita et al. |
| 2003/0139686 A1 | 7/2003 | Rubinstein |
| 2004/0019293 A1* | 1/2004 | Schweitzer et al. ......... 600/549 |
| 2004/0025871 A1 | 2/2004 | Davies |
| 2004/0076215 A1 | 4/2004 | Baumbach |
| 2004/0243021 A1* | 12/2004 | Murphy et al. ............... 600/549 |
| 2005/0043631 A1 | 2/2005 | Fraden |

| | | | | | | | |
|---|---|---|---|---|---|---|---|
| 2005/0211436 | A1 | 9/2005 | Fripp et al. | WO | 2006009585 A1 | 1/2006 | |

OTHER PUBLICATIONS

FOREIGN PATENT DOCUMENTS

| | | | |
|---|---|---|---|
| DE | 2913048 | A1 | 10/1980 |
| EP | 0747682 | A1 | 12/1996 |
| WO | 96/19938 | A1 | 7/1996 |

U.S. Patent and Trademark Office, Office Action in U.S. Appl. No. 10/870,654, Mar. 27, 2007.

European Patent Office, Supplementary European Search Report in EP Application No. EP05713646, May 28, 2009.

* cited by examiner

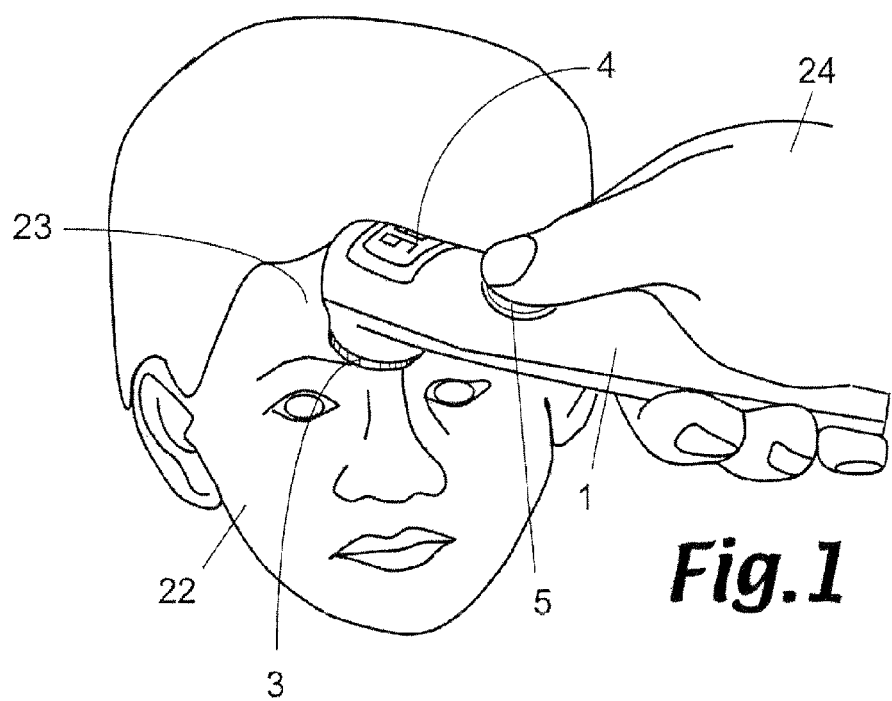
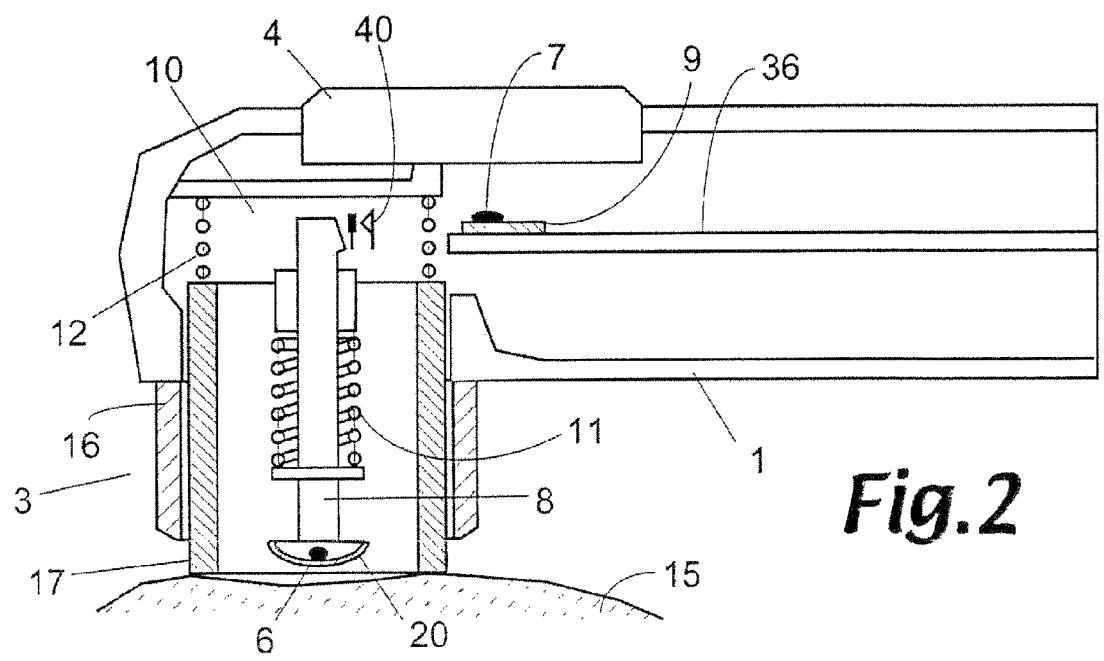

MEDICAL BODY CORE THERMOMETER

This application is a continuation of PCT Application Serial No. PCT/US2005/004884 filed Feb. 16, 2005 which is a continuation-in-part of U.S. application Ser. No. 10/870,654, filed on Jun. 18, 2004, now pending, and claims the priority of provisional patent application Ser. No. 60/495,952, filed Aug. 19, 2003 (abandoned). The disclosures of each of these prior related applications are hereby fully incorporated by reference herein.

FIELD OF THE INVENTION

This invention relates to medical thermometers. More particularly, the invention relates to thermometers that determine core body temperature.

BACKGROUND OF THE INVENTION

Body temperature is universally accepted as an important indicator of the physical condition of humans and other warm blooded animals. For many years, the most common method of measuring body temperature was to insert a contact type thermometer into the patient's mouth or rectum relying on conduction of heat to register an accurate temperature. One such thermometer is a mercury-in-glass thermometer. These thermometers are potentially hazardous due to a possibility of a mercury spill and glass breakage. An alternative contact type thermometer is an electronic "pencil" thermometer. These traditional thermometers will not register a body temperature until after they are left in the patient's mouth, rectum or other location for a relatively long time, thus making the measurement slow and uncomfortable.

A more advanced instrumentation has been developed for measuring the human body temperature by non-contact readings of the infrared (IR) emissions from the tympanic membrane and the ear canal. That is, the IR sensor element takes a reading without the sensor or associated sensing elements having to contact the patient. This technology has been the subject of patents to O'Hara et al. (U.S. Pat. No. 4,790,324) and Fraden (U.S. Pat. No. 4,854,730). The determination of body temperature from an IR reading of the ear drum or ear canal avoids a need of insertion of a probe into a mouth or rectum and allows a measurement of body temperature within a few seconds. However, the IR thermometers have their own problems, the most important of which is susceptibility to the operator's technique of taking a temperature. Other drawbacks include effects of ambient temperature and sensitivity to cleanliness of the IR lens. The IR thermometers are also relatively expensive.

Another IR thermometer, which is exemplified by U.S. Publication No. 2002/0114375 by Pompei, describes estimation of a core temperature by measuring the skin temperature and the ambient temperature by use of an IR emission detector. This method, however, suffers from other limitations, including an operator's technique, higher cost and other factors.

Any traditional contact (non-IR) thermometer has a probe with a temperature sensor that responds to temperature of an object, i.e., a thermal temperature sensor. The rate of response depends on the degree of a thermal coupling with the object, nature of an object, the sensor's isolation from other components and its thermal capacity. There are two known techniques in the art of a contact thermometry. One is the equilibrium and the other is the predictive technique. The equilibrium demands a sufficiently long time to allow the sensor to stabilize its response, meaning that the sensor's temperature and the object's temperature become nearly equal. The predictive technique is based on measuring the rate of the sensor's response and estimation of its would be equilibrium level which is not actually achieved during the measurement but rather anticipated mathematically. The latter technique allows a much quicker measurement but can result in some loss in accuracy. The predictive method is exemplified by U.S. Pat. No. 3,978,325. Some of the predictive techniques rely on a software data processing, while others rely on a hardware design. For instance, U.S. Pat. No. 3,872,726 issued to Kauffeld et al. teaches forecasting the ultimate temperature of a slow responding thermistor in a contact thermometer by using a hardware integrator. These thermometers are still intended for insertion into a body orifice.

It is therefore an object of the present invention to provide an electronic thermometer that can register a core body temperature of a mammal without necessarily being inserted in the mouth or rectum.

It is another object of the present invention to provide an electronic thermometer that can register a core or internal body temperature of a warm blooded animal or human patient quickly after contacting the patient's skin.

It is another object of the present invention to provide a thermometer that determines core body temperature in a manner that is less dependent on the operator's technique.

It is another object of the invention to provide an inexpensive thermometer which is easy to manufacture.

Further and additional objects are apparent from the following discussion of the present invention and the preferred embodiment.

SUMMARY OF THE INVENTION

In one general embodiment, the present invention provides a temperature sensing device operative to determine the core temperature of a warm blooded animal or human based on at least one measurement of the temperature of the skin of the warm blooded animal or human. The device comprises a housing, and a first contact type temperature sensing element coupled to the housing. The first contact type temperature sensing element includes a first temperature sensor that is operative to measure the temperature of the skin when the first temperature sensing element is in contact with the skin. The first temperature sensor produces at least a first signal. An electronic circuit uses the first signal to determine the core temperature of the warm blooded animal or human. An electronic communication device, such as a visual display or audio device, is coupled to the electronic circuit for communicating the core temperature to a user.

In an additional aspect of the invention, a thermal insulator is positioned adjacent the first temperature sensor. Also, a second temperature sensor may be coupled to the housing, and if this aspect of the invention is utilized, the thermal insulator is positioned generally between the first and second temperature sensors so as to thermally decouple the first and second temperature sensors from each other. The second temperature sensor is positioned so as to be thermally decoupled from the skin during thermal measurement of the skin with the first temperature sensor and the second temperature sensor detects a reference temperature represented by at least a second signal. The electronic circuit then uses the first and second signals to determine the core temperature.

In another aspect of the invention, a moveable element carries the first contact type temperature sensing element. The moveable element is configured to be moved into at least first and second positions. The first position is a position at which the first contact type temperature sensing element is not adapted for contact with the skin of the patient and the second position is a position at which the first contact type temperature sensing element is adapted for contact with the skin of the patient. The moveable element can further comprise a shaft formed from a thermally insulating material, and this shaft may be spring loaded to normally bias the first contact type temperature sensing element toward the first position, that is, out of contact with the skin.

A guard may be coupled to the housing according to another aspect of the invention. The guard is configured to surround and protect the first contact type temperature sensing element when not in use. The guard can be moveable relative to the first contact type temperature sensing element to allow the first contact type temperature sensing element to contact the skin while measuring the temperature of the skin.

In another embodiment of the invention, a temperature sensing device operative to determine the core temperature of a warm blooded animal or human comprises a housing and a temperature sensor coupled to the housing. A power supply is coupled to the temperature sensor, and an electronic circuit is electrically coupled to the temperature sensor and the power supply. The electronic circuit operates to determine the core temperature using at least one reading taken from the temperature sensor. An electronic communication device is coupled to the electronic circuit and operates to communicate the core temperature to a user. A handling detector is coupled with the power supply and operates to detect handling of the device by the user and, in response, activate the supply of power from the power supply to the electronic circuit. As examples, the handling detector can further comprise various types of motion sensors, such as tilt detectors, or may be touch sensitive, such as through the use of a capacitive touch sensor. Redundant systems of this type may be used if desired to ensure that the device powers up upon handling by the user. Another possibility is to provide a switch mechanically coupled to the temperature sensor such that, for example, if the sensor or portion carrying the sensor is tapped on a table or counter surface, the device will power up.

The invention further contemplates methods for determining the core temperature of a warm blooded animal or human based on at least one measurement of the temperature of the skin of the warm blooded animal or human. Generally, the method involves contacting the skin of the warm blooded animal or human with a first contact type temperature sensing element. The temperature of the skin is then determined based on at least a first signal from the first contact type temperature sensing element. The first signal is then used to determine the core temperature of the warm blooded animal or human.

The method can further involve determining the temperature of the first contact type temperature sensing element prior to determining the temperature of the skin with the first contact type temperature sensing element. At least a second signal is produced representative of the temperature of the first contact type temperature sensing element. The first and second signals are then used to determine the core temperature of the warm blooded animal or human.

In another aspect of the invention, determining the temperature of the skin further comprises measuring a rate of change in skin temperature readings.

Another aspect of the invention involves producing at least a second signal representative of the temperature of a second thermal temperature sensor thermally insulated from both the first contact type temperature sensing element and the skin, and using the first and second signals to determine the core temperature of the warm blooded animal or human.

Various additional aspects and features of the invention will become more readily apparent to those of ordinary skill upon review of the following detailed description of the illustrative embodiments.

BRIEF DESCRIPTION OF DRAWINGS

FIG. 1 is a perspective view of a first illustrative embodiment of a thermometer in accordance with the invention and shown with a probe touching the skin of the patient's forehead.

FIG. 2 is a cross-sectional view of the thermometer of FIG. 1 with two absolute temperature sensors and a spring-loaded thermal contact mechanism.

DETAILED DESCRIPTION OF THE PREFERRED EMBODIMENTS

Two major issues of a patient core temperature measurement are addressed by this invention. The first is the speed of response (i.e., the speed at which an accurate temperature is displayed) and the second is a non-invasive measurement with an acceptable accuracy. The thermometer is intended for intermittent measurements of temperature by touching a selected location on the skin of a patient's body.

Figure 3:
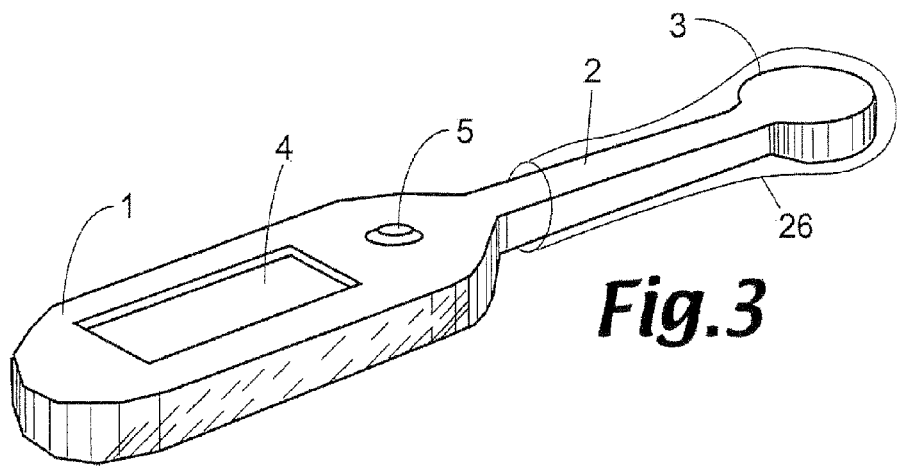
FIG. 3 shows another embodiment of a thermometer with a probe enveloped by a probe cover.

One form of the thermometer is shown in FIG. 1. The device has a housing 1 that can be held by a user's hand 24. Optional switch 5 can be used to power up the device and take a measurement. The result of measurement is represented on a display 4. Probe 3 touches skin (for example, forehead 23) of patient 22. FIG. 3 shows another embodiment of the thermometer that has an elongated neck 2 and probe 3 which are enveloped by sanitary probe cover 26 that can be of a conventional design. Usually, the probe covers 26 are narrow elongated bags fabricated of thin polymer film having thickness on the order of 0.001 inch.

This thermometer is intended for temperature measurements from such body sites as a carotid artery region behind the ear lobe, tragus area (near the ear), armpit, chest, abdomen, groin, and forehead. Design of a practical probe will be influenced by a selected measurement site. The basic design principles are exemplified for a forehead probe and in pertinent part will be applicable for other body site probes.

FIG. 2 shows a cross-sectional view of housing 1 and probe 3. Housing 1 contains a first contact type temperature sensor 6, a second thermal temperature sensor 7 and a thermal insulator 10 positioned between the two sensors 6, 7. The insulator 10 may be fabricated of any conventional insulating material or it may be just void or air space between the two sensors as shown in FIG. 2. The sensors 6, 7 are preferably absolute temperature sensors such as NTC thermistors, semiconductors, or RTDs. Here, the term "absolute" means that they can measure temperature with reference to an absolute temperature scale. Naturally, other types of sensors can be employed, such as thermocouples. However, a thermocouple being a relative sensor would require use of an absolute reference sensor. Below, thermistors are described to illustrate the operating principle. First sensor 6 is intended for coming into a thermal contact with the patient skin (in this example, via plate 20), while second sensor 7 is thermally insulated from the patient at all times. Note that sensor 7 is optional and is not essential for the operation. However, it may aid in enhancing accuracy and thus may be used if needed in a particular design.

For stabilizing a thermal response, sensor 7 is attached to thermal mass 9 (a metal plate). Thermal mass 9 may be supported by a circuit board 36. Likewise, sensor 6 can be attached to plate 20 that is also fabricated of metal to form a temperature sensing element. It is important to provide a good thermal coupling between first sensor 6 and plate 20. Plate 20 may be fabricated of copper having a thickness on the order of about 0.010" and gold plated to prevent oxidizing that may result from touching the patient's skin. For better coupling with the skin, plate 20 can have a convex shape. Of course, the temperature sensing element may take many alternative forms.

Figure 4:
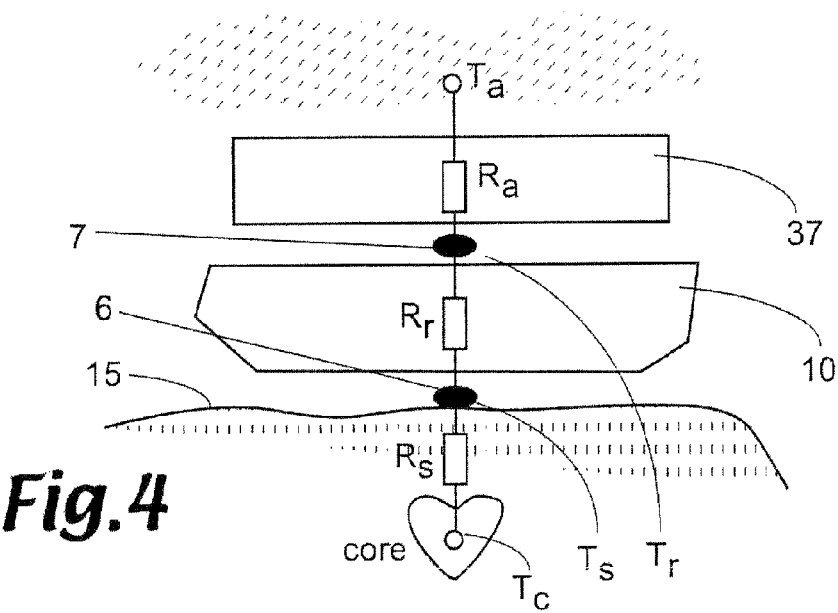
FIG. 4 is a thermal diagram of the thermometer of FIG. 1 with a temperature sensing element touching the skin.

To improve the consistency of thermal contact with the patient's skin, plate 20 may be made movable. More preferably, plate 20 may be supported by shaft 8 that is mechanically connected to first spring 11 and can move in and out of probe 3. The spring 11 helps to assure a steady, constant and reliable pressure applied by plate 20 to skin 15. Shaft 8 is preferably fabricated of a material with low thermal conductivity and preferably should be made hollow (see FIG. 5). Shaft 8 may serve the function of thermal insulator 10 (FIGS. 2 and 4). Both sensors, 6 and 7, are connected to the electronic components on circuit board 36 via conductors that are not shown in FIG. 2.

To protect a delicate probe tip (plate 20 and shaft 8) while using it or while it is in storage, another movable component or guard 17 may be employed (FIG. 2). Guard 17 is pushed downward by a second spring 12. Guard 17 can move in and out of sleeve 16. Guard 17 and sleeve 16 may be fabricated of plastic and positioned in spaced relation to plate 20 as shown in FIG. 2. The edge of guard 17 that comes in contact with the skin, can be rubberized to minimize slippage while in use. When probe 3 is not touching skin 15, guard 17 is protruding from sleeve 16, thus shielding plate 20 from possible mechanical damage. When probe 3 comes in contact with skin 15 and a sufficient pressure is applied, guard 17 slides inside sleeve 16, thus exposing plate 20 and allowing it to come in contact with skin 15. Further pressure compresses both springs 11 and 12 until guard 17 reaches its limit of movement. This provides a predetermined degree of the first spring 11 compression and aids in consistency of measurements.

FIG. 4 illustrates the basic principle of measuring core temperature according to an illustrative embodiment of the invention. When probe 3 is pressed against patient's skin 15, first temperature sensor 6 becomes thermally coupled to the patient core through the patient body thermal resistance $R_s$. The core or internal body temperature is represented as $T_c$. The value of $R_s$ depends on thermal properties of skin, fat, muscles, etc. It should be kept in mind that this resistance is not constant, even for the same patient. It is affected by the ambient and patient temperatures, patient's age, clothing, etc. In fact, this resistance is under a constant physiological control by the patient's central nervous system. Temperature distribution within the probe depends on the thermometer housing temperature $T_a$, force of the plate 20 (FIG. 2) compression, thermal insulator 10 and any outer insulator 37 which is formed by the components inside the thermometer housing 1.

Reference temperature $T_r$ is measured by second sensor 7. When the skin is touched by the probe 3, and specifically by plate 20, heat flows from the patient's core to the thermometer housing via thermal resistances $R_s$, $R_r$, and $R_a$ (thermal resistance of outer insulator 37). Since resistance $R_s$ is not fixed, a true core body temperature computation is impossible. However, an accurate approximation by a 2nd order equation can provide results with an acceptable degree of clinical accuracy. Equation (1) provides a practical way to compute a deep body (core) temperature from temperature of skin $T_s$ and reference temperature $T_r$:

$$T_c = AT_s^2 + (B+CT_r)T_s + DT_r + E \qquad \text{Equation (1)}$$

where A, B, C, D and E are the experimentally determined constants.

To determine the constants (A-E), temperatures from a relatively large number of patients (30 or more) are measured with the thermometer of this invention (hereinafter "device under test" or "DUT") and a reference thermometer of a conventional design. The reference thermometer must have an acceptable degree of accuracy of measuring the body core temperatures. An example is an infrared ear (tympanic) thermometer. Since it is a well known fact that skin temperature is affected by ambient temperatures (see, for example Y. Houdas and E. F. J. Ring. *Human Body Temperature*. Plenum Press, New York and London. 1982), the experiments are made while the patients and the thermometers are subjected to cold, warm and normal room temperatures. Three constants (A, B and C) are inversely related to a patient's physiological limit of temperature ($T_L$). The value of $T_L$ corresponds to the highest controllable temperature of a human body that can be tolerated without irreversible damage to the internal organs. For all practical purposes it is determined as 42° C. If the measurement site is selected on a neck over a carotid artery of an adult, before collecting data, values of the constants in DUT are initially set as:

$A = 1/T_L$ $B = 1 + 15/T_L$ $C = -0.2/T_L$ $D = -0.25$ $E = -22$

Then, data are collected from many patients and a well known in the art curve fitting technique is employed to the ensemble of temperature data. The goal of the curve fitting is to minimize differences between the DUT and the reference thermometer readings, by adjusting values of the constants. This should be done separately for different patient age groups. Other anatomical factors may also be taken into account. The constants will be different for different body sites (forehead, tragus area, etc.). After the constants are adjusted, they can be used in operating a practical thermometer according to the inventive principles.

It is important to note that in Equation (1), $T_s$ represents a true skin temperature, yet first sensor 6 may not be able to quickly measure the true skin temperature while touching skin 15. The reason is that skin is a poor heat conductor and has a rather low thermal capacity. Thus, touching skin 15 with plate 20 for a short time alters the skin temperature from a true value of $T_s$ to some measured value $T_p$. Hence, before Equation (1) can be employed, the value of a true skin temperature $T_s$ should be computed. This can be done by using two temperatures: $T_0$ and $T_p$, where $T_0$ is the temperature of first sensor 6 before touching skin 15. This temperature is referred to as the baseline temperature. It depends on many factors, specifically, the materials used in the probe, the ambient temperature, and the history of use, i.e., how recently the probe touched the skin. For computation of $T_s$, Equation (2) provides a sufficient accuracy:

$$T_s = (T_p - T_0)\mu + T_p \qquad \text{Equation (2)}$$

where $\mu$ is the experimentally determined constant. To finds the value of $\mu$, multiple skin temperature measurements are made with varying $T_0$ and then a value of $\mu$ is selected to minimize effects of $T_0$ on $T_s$. For example, $\mu=0.5$.

Figure 5:
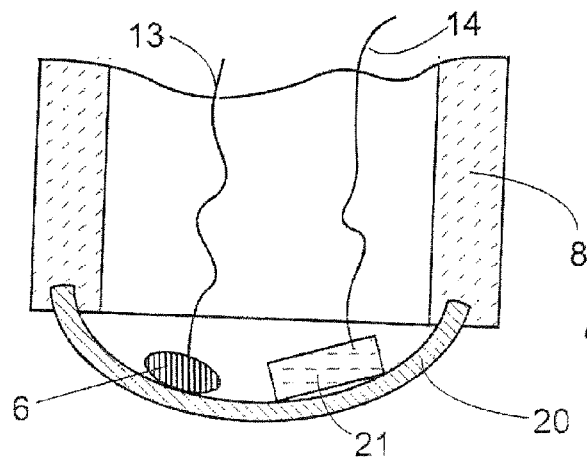
FIG. 5 is a partial cross section of an alternative temperature probe having a heater.

If shaft 8 has a very low thermal conductivity and plate 20 has very low thermal capacity, the temperature measurement time may take less than about 3 seconds. However, when the probe tip is cold (baseline temperature $T_0$ is low), plate 20 may alter the skin temperature so much that it may take a longer time to measure and compute temperature $T_p$. To further shorten the response time of first sensor 6, the probe tip can be pre-warmed by an embedded heater 21 as illustrated in FIG. 5. Heater 21, first sensor 6 and plate 20 are in an intimate thermal coupling with each other. Heater 21 and first sensor 6 are connected to the electronic circuit by conductors 14 and 13, respectively. Before the skin is contacted by plate 20, heater 21 elevates temperature of plate 20 to a level that is warmer than ambient and somewhat below an anticipated skin temperature. A good practical number for a pre-warming is 28° C. (82° F.). This pre-warmed temperature will be used in Equation (2) as $T_0$. The heater is preferably turned off before or at the instant when skin is being touched.

Figure 6:
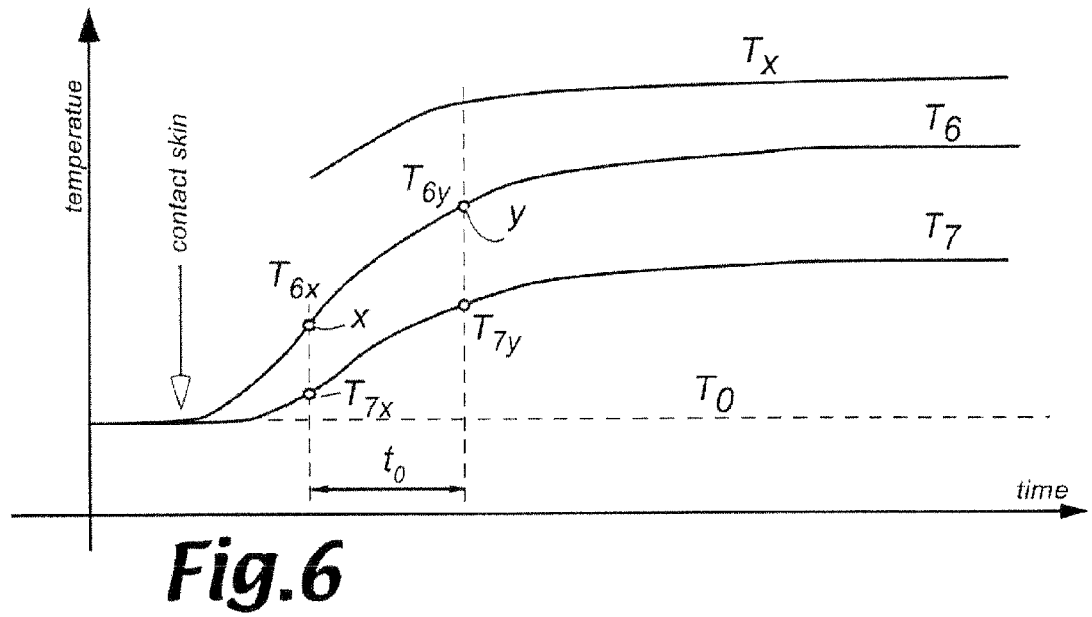
FIG. 6 illustrates a timing diagram of sensor response upon contact between the probe and the skin.

Before Equation (2) can be used for calculating the skin temperature $T_s$, an accurate determination of the first sensor 6 temperature $T_p$ is made. This task, however, typically cannot be accomplished by just measuring and computing temperature of first sensor 6. The reason is that the temperature of sensor 6 changes rather quickly and its output signal keeps changing for an extended period of time. After the skin is touched, the heat flow from the subcutaneous tissues (carotid artery, e.g.), through the skin, to plate 20 and further through shaft 8 (which serves as a thermal insulator 10) will change with a variable rate. FIG. 6 illustrates that the temperatures of both sensors 6 and 7 change over time, while the temperature of first sensor 6 varies much more. The change in heat flow will continuously modify the temperature of the skin at the contact spot and that of first sensor 6 until a steady-state level $T_p$ is reached. In practice, settling on a steady-state level $T_p$ may take as long as a minute—a very long time indeed. An aspect of this invention shortens the computation time dramatically. For example, with the present invention, $T_p$ may be arrived at within a second rather than a minute. To speed up determination of $T_p$, the following technique is employed.

First, a rate of heat flow through shaft 8 is determined. The rate is measured by taking multiple readings from sensor 6 as shown in FIG. 6. After the temperature detected by sensor 6 starts moving from the base level $T_0$ (upon touching the skin), pairs of data points are selected from a series of readings. Multiple pairs of data points (temperatures at points x and y) from the sensor 6 should be taken over time delays to. It is important that the time delay $t_0$ between points x and y is constant and known. Next, Equation (3) is employed to determine the rate of heat flow:

$$T_{pj} = \frac{T_{6y} - kT_{6x}}{1 - k}, \qquad \text{Equation (3)}$$

where k is a constant. Typically it is equal to 0.5 for $t_0=500$ ms, $T_{6x}$ and $T_{6y}$ are the temperatures measured at points x and y respectively.

Second, multiple values of $T_{pj}$ are computed from a series of pairs x and y and compared with one another. When the difference between two adjacent $T_{pj}$ becomes small, these two values of $T_{pj}$ are averaged and the result $T_p$ is used in Equation (2). If second sensor 7 is employed and its temperature changes as well (as in FIG. 6), a similar technique can be employed to compute $T_r$ from second sensor 7.

Figure 7:
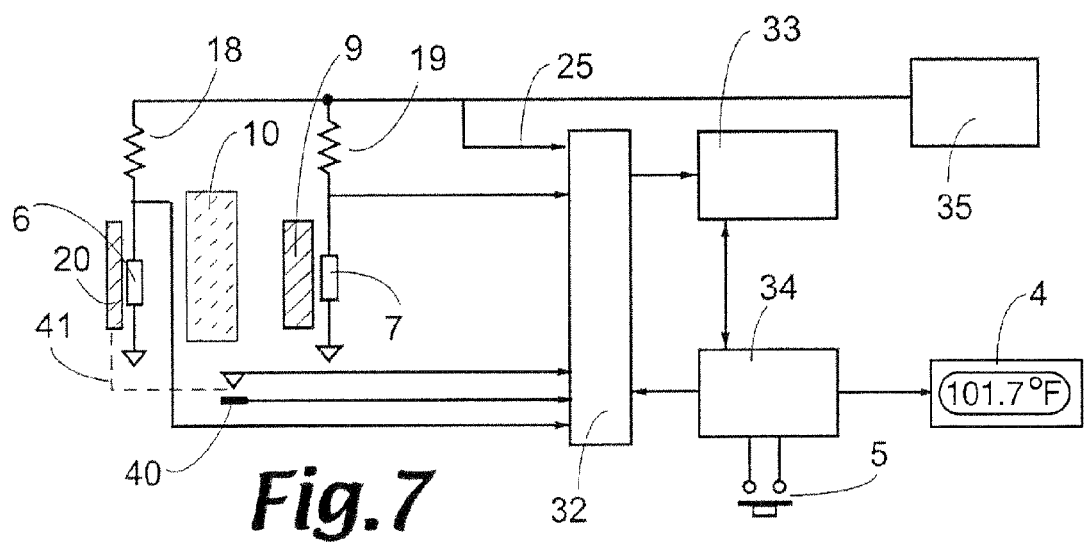
FIG. 7 is a block diagram of the thermometer with two temperature sensors.

FIG. 7 shows a block diagram of a thermometer in accordance with an embodiment of this invention. Two thermistors are used as respective first and second sensors 6, 7. They are pulled up by first and second pull-up resistors 18 and 19, respectively, that are connected to a constant reference voltage 25 generated by power supply circuit 35. Signals from both sensors 6, 7 are fed into a multiplexer 32 which is a gate to allow passage of only one signal at a time. The output signal of multiplexer 32 is applied to an analog-to-digital (A/D) converter 33. All these parts are under control of microcontroller 34, electric power to which can be turned on by switch 5. The result of the core temperature computation is presented on display 4. It should be understood that a similar but modified circuit may be used with a probe having different types of sensors, such as semiconductors, e.g., and signals from various sensors may be used by microcontroller 34 to compute the body core temperature by employing methods as described above.

Figure 9:
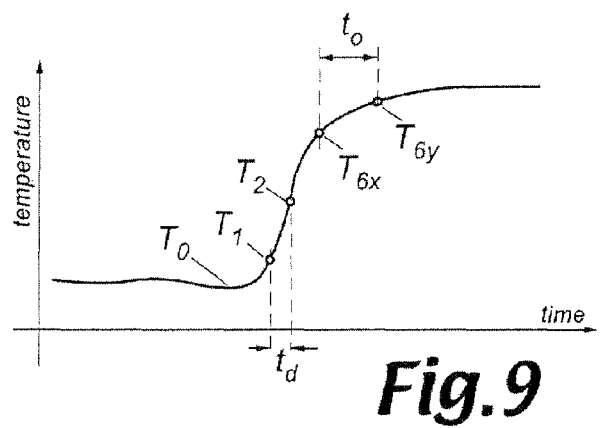
FIG. 9 is a timing diagram of the first temperature sensor response.

There are several ways to detect when plate 20 touches the skin. One way is to use switch 40. To detect the instant when the skin is being touched by plate 20, switch 40 may be mechanically coupled to plate 20 and shaft 8 (FIGS. 2 and 7). When shaft 8 moves, switch 40 closes and sends a signal to microcontroller 34, thus indicating that the skin was touched. If the use of a switch 40 is not desired, other ways to detect touching the skin may be used. For example, after power up, microcontroller 34 can constantly check temperatures of sensor 6 at predetermined time intervals $t_d$ (FIG. 9). A temperature of first sensor 6 stays on a relatively stable level until the probe touches the patient's skin. At this moment, temperature of first sensor 6 begins to rise sharply. A difference between temperatures $T_1$ and $T_2$ is detected to be larger than earlier and this event signals the microcontroller that the skin was touched and the measurements and computation must start.

Figure 8:
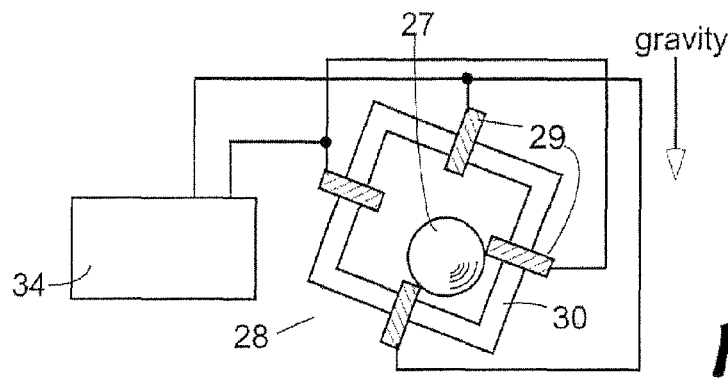
FIG. 8 is a cross-sectional view of a thermometer with a handling detector in the form of a motion detector for automatic power-up.

To make the thermometer more user-friendly, some of its functions can be automated. For example, power switch 5 can be eliminated entirely. Power to the circuit may be turned on automatically by a handling detector when the device is picked-up by a user. FIG. 8 illustrates a simple motion detector 28 that is gravity operated. It has several electrodes 29 embedded into a hollow capsule 30. Electrically conductive ball 27 resides inside capsule 30. When the position of the device changes after being picked up, ball 30 rolls inside capsule 30 making intermittent contact with the internal electrodes 29. This modulates electrical resistances between the adjacent contacts and can be detected by microcontroller 34, signaling it to turn power on. Alternatively, or in addition, housing 1 of the thermometer may have metal contacts on its outer surface that would be part of a capacitive touch sensor. Such a touch sensor may turn on the power similarly to the motion sensor 28 described above. These are just well known examples of various sensors that may be referred to as "handling detectors." Many such detectors or sensors are known in art and thus not described in further detail herein. Some of these detectors are described in a book by Jacob Fraden "*Handbook of Modern Sensors*" ($3^{rd}$ ed., Springer Verlag, NY, 2004) herein incorporated by reference. Note that switch 40 also may be employed as a handling detector for turning power on. When power is off, the probe 3 may be tapped on a surface, such as a table surface. This would momentarily close switch 40, signaling the microcontroller that the measurement cycle may start.

As merely one illustration of the inventive principles, the thermometer of FIG. 7 operates as follows. Initially, the thermometer typically is in storage, such as in a medicine cabinet and its power is off. After being picked-up, motion detector 28 (not shown in FIG. 7) turns power on and temperatures from both sensors 6 and 7 alter the thermistor resistances. Signals from the sensors 6, 7 are fed into multiplexer 32 and then pass to A/D converter 33. Temperatures of sensors 6 and 7 are measured and computed continuously with a predetermined rate. The temperature of first sensor 6 ($T_o$), before the skin is touched, is stored in memory and will be used later for computing the skin temperature $T_s$ by use of Equation (2). The temperature of second sensor 7 is measured and stored as $T_r$. To take a reading, the user pushes the probe tip against the patient's skin and switch 40 closes, indicating the moment of skin touching. The temperature of first sensor 6 rises and is read continuously in a digital format by A/D converter 33. From each pair of the first sensor readings separated by $t_o$, a heat flow rate of change is measured and computed from Equation (3). When microcontroller 34 determines that the rate of change has reached a sufficiently steady value, it computes $T_p$ as described above and subsequently employs Equation (2) to compute the skin temperature $T_s$. Then, using Equation (1), the patient's core temperature $T_c$ is finally computed by using constants, obtained as described above, and stored in the internal memory. The entire process may take only a few seconds from the moment of skin touching.

Some additional computations may also be performed to aid in usefulness of the device. These may include changing the display scale, testing the temperature limits, checking the power supply, etc. Power of the thermometer may be turned off automatically by microcontroller 34 after a preset delay of, for example, 60 seconds.

Figure 10:
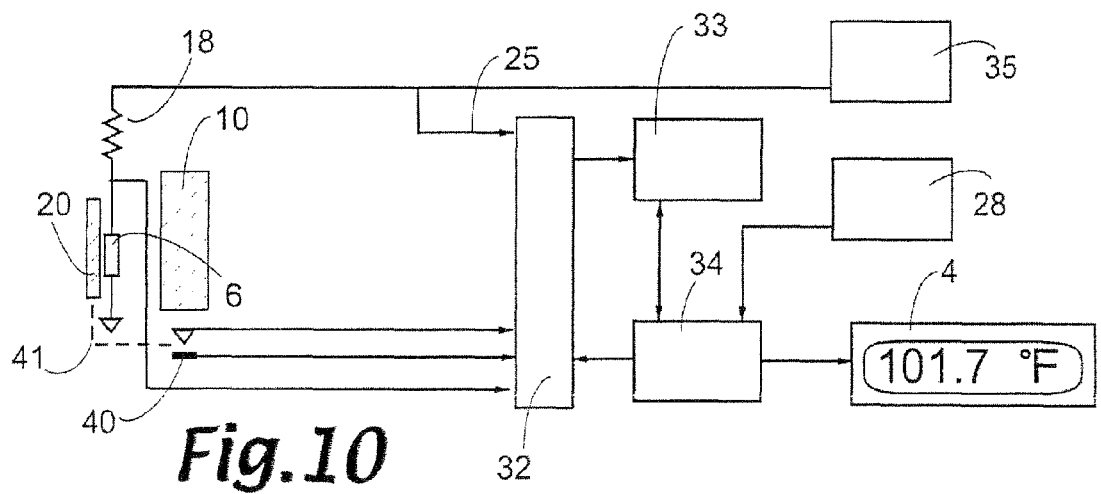
FIG. 10 is a block diagram of another embodiment of a thermometer having a single temperature sensor.

In another embodiment of the invention, only one temperature sensor is used (first sensor 6). This is illustrated in FIG. 10. Since the second temperature sensor 7 is absent, its function is taken over by first temperature sensor 6. Operation of the circuit of FIG. 10 is nearly identical to that of FIG. 7, except that reference temperature $T_r$ is measured by first sensor 6 after power up, as a first control operation, and stored in the internal memory (not shown) of microcontroller 34 for later use in Equation (1).

While the present invention has been illustrated by a description of various preferred embodiments and while these embodiments have been described in some detail, it is not the intention of the Applicant to restrict or in any way limit the scope of the appended claims to such detail. Additional advantages and modifications will readily appear to those skilled in the art. The various features of the invention may be used alone or in numerous combinations depending on the needs and preferences of the user. This has been a description of the present invention, along with the preferred methods of practicing the present invention as currently known. However, the invention itself should only be defined by the appended claims.

I claim:

1. A temperature sensing device operative to determine the body temperature of a warm blooded animal or human based on at least one measurement of the temperature of the skin of the warm blooded animal or human, the device comprising:
   a housing;
   a first contact type temperature sensing element being adapted for contacting the skin and including a first temperature sensor, the first temperature sensor operative to measure the temperature of the skin when the first contact type temperature sensing element is in contact with the skin and produce at least a first signal;
   a moveable element coupled to said housing and carrying the first contact type temperature sensing element, the moveable element configured to be moved relative to the housing into at least first and second positions, the first position being a position at which the first contact type temperature sensing element is adapted to not contact the skin and the second position being a position at which the first contact type temperature sensing element is adapted for contact with the skin for consistent contact with the skin;
   a guard coupled to the housing and being moveable relative to the moveable element, the guard shielding the first contact type temperature sensing element, the guard configured to retract proximally relative to the first contact type temperature sensing element to unshield the first contact type temperature sensing element while the guard is pressed against the skin to bring the first contact type temperature sensing element in thermal contact with the skin;
   an electronic circuit electrically coupled with the first contact type temperature sensing element and operative to use the first signal to determine the body temperature of the warm blooded animal or human; and
   an electronic communication device coupled to the electronic circuit and operative to communicate the body temperature to a user.

2. The device of claim 1, further comprising a thermal insulator positioned adjacent the first temperature sensor.

3. The device of claim 2, further comprising:
   a second temperature sensor coupled to the housing, the thermal insulator positioned generally between the first and second temperature sensors so as to thermally decouple the first and second temperature sensors from each other, and the second temperature sensor further being positioned so as to be thermally decoupled from the skin during measurement of the skin with the first temperature sensor, the second temperature sensor operative to detect a reference temperature represented by at least a second signal, and wherein the electronic circuit uses the first and second signals to accurately determine the body temperature.

4. The device of claim 1, wherein the moveable element further comprises a shaft formed from a thermally insulating material.

5. The device of claim 4, wherein the shaft is spring loaded to normally bias the first contact type temperature sensing element toward the second position.

6. The device of claim 1, further comprising:
   a heating element thermally coupled to said first temperature sensor wherein the heating element generates heat prior to the first temperature sensor being placed in the second position.

7. The device of claim 4, wherein the shaft is aligned along an axis and the moveable element is configured to move the first contact type temperature sensing element away from the housing along the axis.

8. A temperature sensing device operative to determine the body temperature of a warm blooded animal or human, comprising:
- a housing;
- a temperature sensor carried by a moveable element coupled to the housing for movement relative to the housing, the moveable element configured to move temperature sensor from a first position in which the temperature sensor is adapted to not contact the skin of the warm blooded animal or human to a second position in which the temperature sensor is adapted to contact the skin for consistent contact with the skin;
- a guard coupled to the housing and being moveable relative to the moveable element, the guard shielding the temperature sensor, the guard configured to retract proximally relative to the temperature sensor to unshield the temperature sensor while the guard is pressed against the skin to bring the temperature sensor in thermal contact with the skin;
- a power supply coupled to the temperature sensor;
- an electronic circuit electrically coupled to the temperature sensor and the power supply, and operative to determine the body temperature using at least one reading taken from the temperature sensor;
- an electronic communication device coupled to the electronic circuit and operative to communicate the body temperature to a user; and
- a handling detector coupled with the power supply and operative to detect handling of the device by the user, and, in response, activate the supply of power from the power supply to the electronic circuit.

9. The device of claim 8, wherein the handling detector further comprises at least one of a motion sensor and a capacitive touch sensor.

10. The device of claim 8, wherein the handling detector further comprises a switch mechanically coupled to the temperature sensor.

11. The device of claim 8, wherein the moveable element comprises a shaft aligned along an axis, the moveable element being configured to move the temperature sensor away from the housing along the axis.

12. A method of determining the body temperature of a warm blooded animal or human, comprising:
- contacting the skin of the animal or human with a guard movably coupled to a housing, the guard shielding a first contact type temperature sensing element;
- moving the first contact type temperature sensing element relative to the guard and the housing to unshield the first contact type temperature sensing element while the guard is pressed against the skin so that the first contact type temperature sensing element is brought into thermal contact with the skin and maintains consistent contact with the skin;
- producing a first signal representative of a temperature of the first contact type temperature sensing element in thermal contact with the skin; and
- using the first signal to determine the body temperature of the animal or human.

13. The method of claim 12, further comprising:
- determining the temperature of the first contact type temperature sensing element while the first contact type temperature sensing element is not contacting the skin;
- producing at least a second signal representative of the temperature of the first contact type temperature sensing element while the first contact type temperature sensing element is not contacting the skin; and
- using the first and second signals to determine the body temperature of the warm blooded animal or human.

14. The method of claim 12, wherein determining the body temperature of the warm blooded animal or human further comprises:
measuring a rate of change of the first signal.

15. The method of claim 12, further comprising:
- producing at least a second signal representative of the temperature of a second temperature sensor thermally insulated from both the first contact type temperature sensing element and the skin; and
- using the first and second signals to determine the body temperature of the warm blooded animal or human.

16. The method of claim 13, wherein the body temperature is determined using the equation $$T_c = AT_s^2 + (B+CT_r)T_s + DT_r + E$$

where: $T_c$ is the core temperature,
$T_S$ is the skin temperature,
$T_r$ is a reference temperature, and
A, B, C, D and E are constants.

17. The method of claim 12, further comprising:
elevating the temperature of the first contact type temperature sensing element prior to contacting the skin with the first contact type temperature sensing element.

18. The method of claim 13, wherein the body temperature is determined using the equation $$T_c = AT_s^2 + (B+CT_r)T_s + DT_r + E$$

where:
$T_c$ is the core temperature,
$T_S$ is the skin temperature,
$T_r$ is a reference temperature, and
A, B, C, D and E are constants.

* * * * *

UNITED STATES PATENT AND TRADEMARK OFFICE
CERTIFICATE OF CORRECTION

PATENT NO. : 7,828,743 B2
APPLICATION NO. : 11/564449
DATED : November 9, 2010
INVENTOR(S) : Jacob Fraden It is certified that error appears in the above-identified patent and that said Letters Patent is hereby corrected as shown below:

Column 7
Line 16, reads "To finds the" and should read -- To find the --.

Column 7
Line 67, reads "time delays to" and should read -- time delays $t_o$ --.

Column 12
Lines 31-37, Claim 16, reads "The method of claim 13, wherein the body temperature is determined using the equation...where: ...is the core temperature, ...is the skin temperature, ...is a reference temperature, and...A, B, C, D and E are constants" and should read -- The method of claim 13, wherein the body temperature is determined using the equation...where: ...is the body temperature (core temperature), ...is the skin temperature computed from the first signal, ...is a reference temperature computeed from the second signal, and...A, B, C, D and E are constants --.

Column 12
Lines 42-51, Claim 18, should be canceled per Amendment dated October 9, 2008 --.

Signed and Sealed this
Eighth Day of March, 2011

David J. Kappos
*Director of the United States Patent and Trademark Office*